US00PP18710P2

(12) United States Plant Patent
Austin

(10) Patent No.: US PP18,710 P2
(45) Date of Patent: Apr. 8, 2008

(54) SHRUB ROSE PLANT NAMED 'AUSVOLUME'

(50) Latin Name: *Rosa hybrida*
Varietal Denomination: AUSvolume

(75) Inventor: David C. H. Austin, Wolverhampton (GB)

(73) Assignee: David Austin Roses Limited, Albrighton, Wolverhampton (GB)

( * ) Notice: Subject to any disclaimer, the term of this patent is extended or adjusted under 35 U.S.C. 154(b) by 0 days.

(21) Appl. No.: 11/635,213

(22) Filed: Dec. 6, 2006

(51) Int. Cl.
*A01H 5/00* (2006.01)

(52) U.S. Cl. ..... Plt./107
(58) Field of Classification Search ..... Plt./107
See application file for complete search history.

*Primary Examiner*—Kent Bell
*Assistant Examiner*—S. B. McCormick-Ewoldt
(74) *Attorney, Agent, or Firm*—Kauth, Pomeroy, Peck & Bailey LLP

(57) ABSTRACT

Shrub rose plant substantially as herein shown and described, characterized particularly by very large, full, cupped, rosette shaped blooms of deep pink color; a good, fruity, Old Rose fragrance; and bushy, upright and very vigorous growth.

1 Drawing Sheet

Genus and species: *Rosa hybrida.*
Variety denomination: 'AUSvolume'.

ORIGIN OF THE INVENTION

The present invention relates to a new and distinct variety of a shrub rose plant named 'AUSvolume' which was originated by me by crossing an unnamed, unpatented seedling with an unnamed, unpatented seedling.

BACKGROUND OF THE INVENTION

The primary objective of this breeding was to produce a repeat flowering, healthy and vigorous variety with large, deep pink blooms and a strong fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Very large, full, cupped, rosette shaped blooms of deep pink color.
2. A good, fruity, Old Rose fragrance.
3. Bushy, upright and very vigorous growth.

Asexual reproduction of this new variety by budding, as performed at Albrighton, England, shows that the foregoing and all other characteristics and distinctions come true to form and are established and transmitted through succeeding propagations.

Comparison with Parents

The seed parent has bright crimson, more loosely formed blooms compared to the deep pink, very full blooms of 'AUSvolume'. The pollen parent has cupped, rich yellow blooms compared with the deep pink, rosette-shaped blooms of 'AUSvolume'.

Comparison with Similar Variety

'AUSintense' (U.S. Plant Pat. No. 16,763) has smaller, paler pink blooms than 'AUSvolume'. 'AUSvolume' has more upright growth and larger, broader leaflets than 'AUSintense'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling (Unpatented).

FLOWER

Observations made from plants commencing at one year of age grown in a garden environment at Albrighton, England.

Blooming habit: Recurrent. The number of blooms per plant during the growing season is profuse — there are too many to count.

Bud:
*Size.*—About 3.5–4 cm long and 2.5 cm in diameter when the petals start to unfurl.
*Form.*—The bud form is broad based.
*Color.*—When sepals first divide, bud color is Red-Purple Group 58B. When half blown, the upper sides of the petals are Red Group 54A with Red Group 50B at the base and the lower sides of the petals are Red-Purple Group N66A with Red Group 50B at the base.

*Sepals.*—Color: Upper surface: Yellow-Green Group 147D. Lower surface: Yellow-Green Group 144A with Yellow-Green Group 144C at the base. Length: 2.6 cm. Width: 1.1 cm. Shape: Subulate. Surface texture: Upper surface: Pubescent. Lower surface: Smooth. There are three very lightly appendaged sepals. There are two unappendaged sepals with canescent edges.

*Receptacle.*—Color: Yellow-Green Group 144A. Shape: Campanulate. Size: Large, about 1.4 cm long×1.2 cm wide. Surface: Smooth.

*Peduncle.*—Length: Medium, averaging about 4–5 cm. Surface: Glandular. Color: Yellow-Green Group 144B overlaid occasionally with Greyed-Orange Group 172B on the sun-facing portion. Strength: Strong.

Bloom:

*Size.*—Very large. Average open diameter is about 10.4 cm.

*Borne.*—Several together in irregular compound corymb clusters of three to four blooms.

*Form.*—When first open: Cupped. Permanence: Flattens, very outer petals curl back.

*Petalage.*—Number of petals under normal conditions: 100.

*Color.*—The upper sides of the petals are Red-Purple Group 61C, basal half overlaid with Red Group 50A. The reverse sides of the petals are Red-Purple Group 67C overlaid with Red Group 50A, becoming more intense toward the base. The base of each petal is Yellow Group 13B.

*Variegations.*—None.

*Discoloration.*—The general tonality at the end of the first day is Red-Purple Group 31C. At the end of the third day: Red-Purple Group 67A.

*Fragrance.*—Strong; Fruit and Old Rose.

Petals:

*Texture.*—Smooth.

*Size.*—Width: 3.4 cm. Length: 4.1 cm.

*Surface.*—Smooth.

*Shape.*—Obcordate (inner petals); obdeltoid (outer petals). Margin: Notched. Apex Shape: Emarginate (outer petals); obcordate (inner petals). Base Shape: Cuneate. Form: Incurved, tips and margin recurved.

*Arrangement.*—Quartered.

*Petaloids.*—Number: 4. Color: Anther: Yellow-Orange Group 15B; Filament: Yellow-Orange Group 15B; Petal: Red Group 53D. Length: Anther: 2 mm; Filament: 5 mm; Petal: 5 mm.

*Persistence.*—Petals drop off cleanly before drying.

*Lastingness.*—On the plant: Fair (about 4 days). As a cut flower: Fair (about 5 days).

Reproductive parts:

*Stamens.*—Number: 56. Length: 7–10 mm. Anthers: Length: 2 mm. Color: Yellow-Orange Group 17B. Arrangement: Regular around styles, mixed with petaloids. Filaments: Color: Yellow-Orange Group 17B. Length: 5–8 mm. Pollen: Color: Yellow-Orange Group 17B.

*Pistils.*—Number: 85–90. Length: 9 mm. Styles: Color: Green-Yellow Group 1D. Length: 8 mm. Stigmas: Color: Yellow Group 3A. Length: 1 mm.

*Hips.*—None observed.

PLANT

*Form.*—Shrub.

*Growth.*—Vigorous, bushy.

*Age at maturity.*—Two years.

*Mature plant.*—Height: 1.2 m. Width: 0.9 m.

*Rootstock.*—'Dr. Huey' in the USA *Rosa dumetorum* 'Laxa' for the observed plants in the U.K.

Foliage: Number of leaflets on normal mid-stem leaves: 5–7 (including terminal leaflet).

*Size.*—Medium. About 17.3 cm long×12 cm wide.

*Quantity.*—Normal. Average number leaves per flowering stem: 10.

*Color.*—New foliage: Upper side: Green Group 143A. Lower side: Green Group 143A, overlaid with Greyed-Orange Group 173A toward margin. Old foliage: Upper side: Some Green Group 137A, some Green Group 139A. Lower side: Yellow-Green Group 147B.

Leaflets:

*Size.*—About 6.6 cm long×4.8 cm wide.

*Shape.*—Pointed oval.

*Base shape.*—Rounded.

*Apex shape.*—Acuminate.

*Texture.*—Smooth, semi-glossy.

*Edge.*—Serrated.

*Serrations.*—Double, small.

*Petiole.*—Color: Yellow-Green Group 144A or 144B. Length: 2.5–3 cm. Width: 2 mm. Surface texture: Smooth.

*Petiole rachis.*—Color: Yellow-Green Group 145B. Underside: With prickles.

*Stipules.*—Length: 3 cm, serrated and glandular. Color: Yellow-Green Group 144A.

*Auricle shape.*—Subulate. Length: 6 mm. Width: 2 mm, tapering to a point. Color: Yellow-Green Group 144A.

*Disease resistance.*—Resistant to powdery and downy mildew, blackspot and rust in normal growing conditions.

*Pest resistance.*—Not tested.

*Vein color.*—Yellow-Green Group 145B.

*Venation pattern.*—Reticulate.

Wood:

*New wood.*—Color: Yellow-Green Group 144A. Bark: Smooth.

*Old wood.*—Color: Yellow-Green Group 144A. Bark: Smooth.

Stems:

*Mature stem.*—Length: 30 cm. Diameter: 5 mm.

*Internode distance.*—6 cm. The above measurements are all variable, depending on growing conditions in a season.

Prickles:

*Quantity.*—On main canes from base: Many, 18 per 5 cm stem length. On laterals from main canes: Ordinary, 6 per 5 cm per stem length.

*Form.*—Concave curved inward.

*Length.*—5–8 mm.

*Color when young.*—Some Green-Yellow Group 1B, some Greyed-Purple Group 185A.

*Color when mature.*—Greyed-Yellow Group 160A.

Small prickles:

*Quantity.*—On main stalks: Many, 20 per 5 cm stem length. On laterals: Many, 12 per 5 cm stem length.

*Color when young.*—Some Green-Yellow Group 1B, some Greyed-Purple Group 185A.

*Color when mature.*—Greyed-Yellow Group 160A. Winter hardiness: Not tested.

I claim:

1. A new and distinct variety of shrub rose plant substantially as herein shown and described, characterized particularly by very large, full, cupped, rosette shaped blooms of deep pink color having a good, fruity, Old Rose fragrance; and bushy, upright and very vigorous growth.

* * * * *

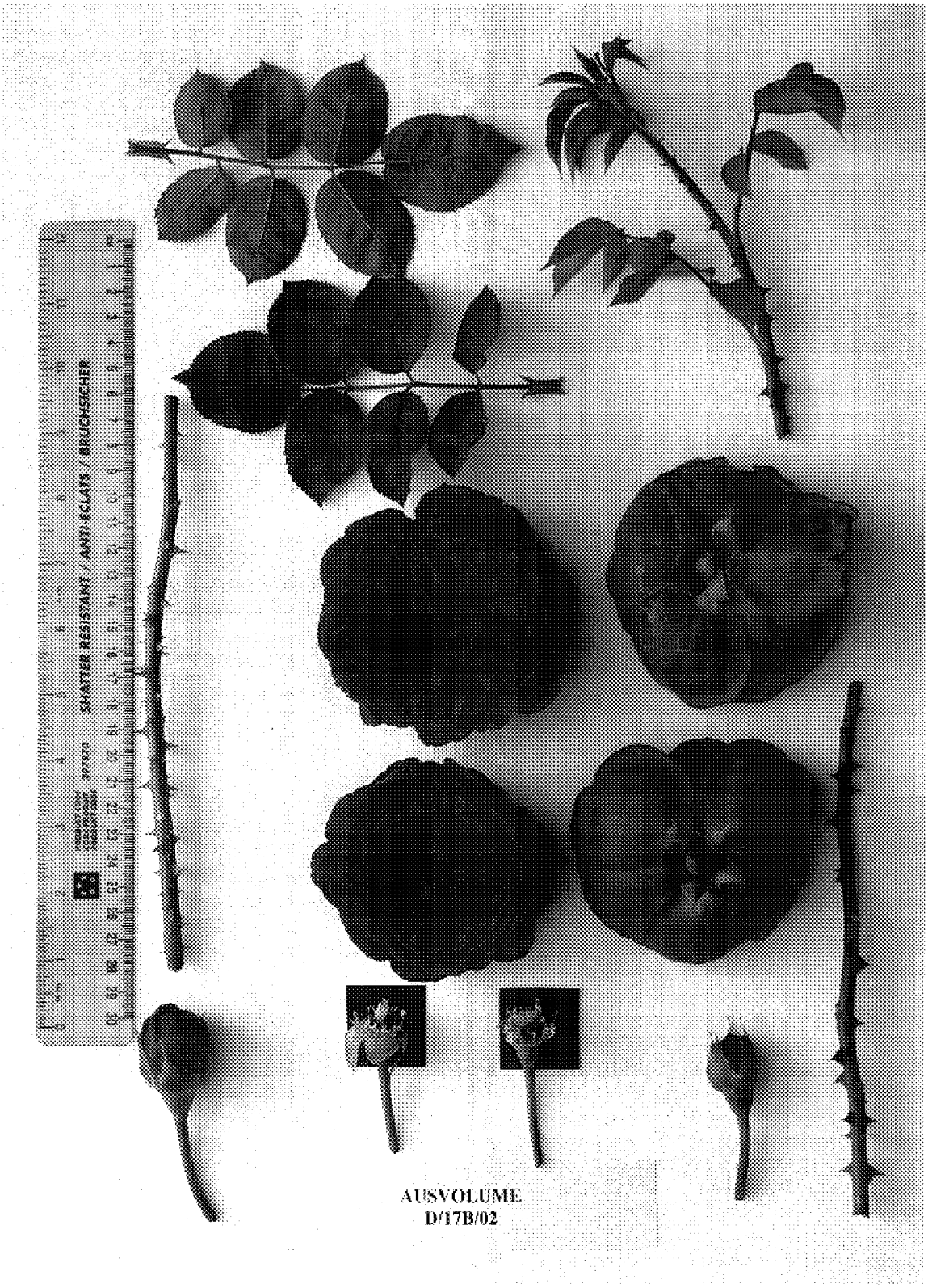
AUSVOLUME
D/17B/02